United States Patent [19]

Masaki et al.

[11] Patent Number: 5,466,464
[45] Date of Patent: Nov. 14, 1995

[54] INTRABUCCALLY DISINTEGRATING PREPARATION AND PRODUCTION THEREOF

[75] Inventors: Katsuhiro Masaki; Kazutoshi Ban, both of Shizuoka, Japan

[73] Assignee: Yamanouchi Pharmaceutical Co., Ltd., Tokyo, Japan

[21] Appl. No.: 256,034

[22] PCT Filed: Dec. 15, 1992

[86] PCT No.: PCT/JP92/01631

§ 371 Date: Jun. 22, 1994

§ 102(e) Date: Jun. 22, 1994

[87] PCT Pub. No.: WO93/12769

PCT Pub. Date: Jul. 8, 1993

[30] Foreign Application Priority Data

Dec. 24, 1991 [JP] Japan .................... 3-356898
Nov. 20, 1992 [JP] Japan .................... 4-335076

[51] Int. Cl.⁶ .................................. A61K 47/26
[52] U.S. Cl. .................. 424/434; 424/439; 424/474; 424/479; 514/960; 514/961; 514/440
[58] Field of Search ..................... 424/440, 439, 424/474, 479, 434; 514/960, 961

[56] References Cited

U.S. PATENT DOCUMENTS 3,419,657  12/1978  Sanders et al. ................... 514/960
5,013,557  5/1991   Tai ............................... 424/439
5,288,497  2/1994   Stanley et al. .................. 424/440

FOREIGN PATENT DOCUMENTS 0379147  7/1990  European Pat. Off. .
1959275  5/1971  Netherlands .
3744009  7/1989  Netherlands .
2009597  6/1979  United Kingdom .

OTHER PUBLICATIONS

Sterling Drug, Inc., *Chemical Abstracts*, vol. 14(16), Apr. 22, 1991, #150194c.

Pharm. Ind. vol. 34, No. 3, 1972 Nuernberg, E. p. 196 Table 6.

*Primary Examiner*—Thurman K. Page
*Assistant Examiner*—Pamela S. Webber
*Attorney, Agent, or Firm*—Burgess, Ryan and Wayne

[57] ABSTRACT

A solid preparation soluble in the buccal cavity, which is composed of a sugar comprising lactose and/or mannitol and 0.1–1.2 w/w%, based on the sugar, of agar and an active ingredient and has a density of 400 to 1,000 mg/ml and such a strength as to withstand the handling in the manufacture thereof. It has such a sufficient practical solubility in the buccal cavity that even the aged or children having difficulty in swallowing a solid preparation, such as a tablet, can take it. It has an exceedingly high strength as compared with conventional open matrix structures and hence can withstand satisfactorily carrying and PTP packaging.

6 Claims, No Drawings

INTRABUCCALLY DISINTEGRATING PREPARATION AND PRODUCTION THEREOF

TECHNICAL FIELD

This invention relates to a solid preparation which has a sufficient handling strength similar to the case of common tablets and also has a practically sufficient solubility or disintegration property in the buccal cavity, and to a process for producing the same.

BACKGROUND ART

Since dosage forms which take into consideration the ease of swallowing by patients are scarce in spite of the existence of various known dosage forms of pharmaceutical preparations for oral administration use, great concern has been directed toward the development of a dosage form which can be easily handled especially by the aged or children who have difficulty in swallowing a solid preparation.

For example, in the case of tablets and capsules frequently used as oral preparations, many aged patients or children having weak swallowing power are unwilling to take these solid preparations complaining that the drug is difficult to swallow or stops in the pharynx or gullet.

In the case of powders and granules, they are difficult to swallow because of their aptness to remain in the buccal cavity and therefore to cause an unpleasant feeling in the mouth. In some cases, the aged will be choked with powders or feel a pain or unpleasantness due to granules lodged between false teeth. In addition, powders and granules have to be used after tearing each package, but the aged or children often have difficulty in tearing the package or spill a portion of its contents.

To take these oral preparations, it is necessary to use water, and the aged or children especially require a large volume of water in many cases because of the swallowing difficulty. However, there is a situation that it is necessary to drink water moderately, especially before retire to bed because of the urination problem at night. In addition, in the case of patients who have to take oral preparations constantly while making daily life, water can hardly be obtained in certain cases depending on circumstances, thus sometimes entailing decline in the compliance.

Syrups and the like are regarded as desirable dosage forms for the aged or children, but the aged or children who have difficulty in measuring the necessary volume cannot be expected to use such preparations in correct dose. In addition, since there are many aged patients who can hardly take liquid preparations by mouth by themselves, such dosage forms cannot always be regarded as suitable dosage forms for the aged and children when trouble at the time of drug-taking is taken into consideration, except for a case in which a patient can ask a nurse for a helping hand.

On the basis of the above, when the forthcoming social condition of advanced age is taken into consideration, development of a dosage form which can be used easily especially by the aged seems to be an immediate need, because the morbidity rate of chronic diseases increases with advance in age and patients of advanced age have a tendency to take drugs for a long period of time. Also, in order to keep the quality of life, it is desirable to develop a dosage form which can be easily swallowed and handled according to the ability and life condition of each patient.

Several pharmaceutical preparations which dissolve or disintegrate in the buccal cavity are known as suitable dosage forms for the aged, children or patients who dislike taking drugs. For example, JP-B-62-50445 discloses a solid preparation having an open matrix network structure which is obtained by freezing an aqueous solution containing gelatin as the main component and a pharmaceutical substance and then sublimating the solvent. (The term "JP-B" as used herein means an "examined Japanese patent publication".) According to this patent publication, the open matrix network structure has a density of 10 to 200 mg/ml and disintegrates rapidly in water within 10 seconds by a tablet disintegration test. It also discloses that spitting of the preparation by patients who dislike drug-taking can be prevented, because the preparation disintegrates rapidly within 1 to 2 seconds in the buccal cavity of the patient and is swallowed together with saliva.

However, because of the rapidly disintegrating property, this open matrix structure has an insufficient strength and is so brittle that its hardness cannot be measured. In consequence, the usual Press Through Pack (blister packaging) and the like from which tablets can be easily taken out cannot be used for this preparation, which therefore requires a specific seal-peeling type packaging, and the preparation is extremely difficult to handle because of its aptness to cause breakage and cracking during its delivery or carrying or when it is taken out from its package at the time of its use. Being sensitive to moisture, it also has a problem of causing stickiness on the surface of the preparation even when it is merely put in the hand. In consequence, this dosage form is not practically appropriate because of its difficulty in handling especially by the aged or children.

JP-A-2-32014 discloses a molded tablet which is produced by temporarily mixing solid components such as sugar, active ingredient and the like with a small volume of a volatile liquid binder sufficient to form a slightly wet lump and putting the thus formed lump into a mold by force to evaporate the liquid binder. (The term "JP-A" as used herein means an "unexamined published Japanese patent application".) However, since this molded tablet is prepared by forced pack molding of a clayey material and drying, air contamination and the like cannot be avoided, thus causing irregularities in the drug content, shape, hardness and the like and entailing inferior practicability. In addition, the production process is not applicable to industrial tablet production, because it requires a special mold packing apparatus.

JP-A-3-56412 discloses an intrabuccally dissolving preparation which is obtained by freeze-drying sugars. However, since this preparation has low hardness, it cannot be applied to conventional Press Through Pack (blister packaging) and has low practicability from the viewpoint of preparation handling. In addition, its production process has low industrial productivity, because the highly viscous suspension to be filled in a mold cannot be applied to the usual liquid filling apparatus, thus requiring a special filling apparatus, and because irregularities in the shape, weight and the like of the final preparation occur.

DISCLOSURE OF THE INVENTION

The inventors of the present invention have conducted extensive studies to develop new dosage forms which can be swallowed easily, handled easily and taken in correct dose and therefore is applicable to the aged and children and, as the result, have succeeded in developing a new dosage form which is easily swallowable without water because of its rapidly disintegrating nature in the buccal cavity and also can easily be handled and taken out from packages.

In addition, this dosage form is excellent in industrial productivity, has uniformity in its drug content and shape and, therefore, is practically useful.

That is, the present invention relates to an intrabuccally disintegrating solid preparation which comprises an active ingredient, a sugar comprising lactose and/or mannitol and 0.12 to 1.2 w/w%, based on the solid components, of agar and which has a density of 400 mg/ml to 1,000 mg/ml and a sufficient strength for the handling. The solid preparation of the present invention has high practicability because of its advantages in that it can be swallowed easily without water due to its rapidly disintegrating nature in the buccal cavity, it has a strength sufficient enough to withstand the handling and, therefore, can be applied to usual Press Through Pack (blister packaging) and the like from which tablets can be taken out easily and it has no particular limitations with regard to its delivery and carrying and its handling after take out from packages.

The present invention also relates to a process for the production of an intrabuccally disintegrating solid preparation having a sufficient strength for the handling, which comprises suspending an active ingredient and a sugar comprising lactose and/or mannitol in a 0.3 to 2.0 w/w% agar aqueous solution used in an amount of 40 to 60 w/w% based on the solid components, filling the suspension in a mold to solidify it into a jelly form, and subsequently drying the jell. According to the inventive production process, the pharmaceutical preparation of the present invention can be produced with excellent uniformities of preparation weight, active ingredient content and shape. In addition, since vacuum drying, aeration drying and the like can be used, the production process is free from complex drying-related operation and therefore is excellent in industrial productivity.

The following describes the present invention in detail.

The sugar which constitutes the preparation of the present invention is lactose and/or mannitol having excellent dispersibility in water and proper solubility. One of these sugars may be used alone or a mixture of them may be used. A structural body having desired hardness and disintegration rate (dissolution rate) can be obtained regardless of their mixing ratio. However, such a structure of interest cannot be obtained when other sugars such as sucrose, glucose, sorbitol and the like are used, and the dissolution rate decreases remarkably even when these other sugars are used in combination with lactose and/or mannitol.

The sugar of the inventive preparation seems to form the desired structural body because the partly dissolved sugar binds the undissolved sugar during the water-removing step which is carried out after solidification of the sugar and an active ingredient under such a condition that the sugar is dispersed in water (partly dissolved). In consequence, the present invention is characterized in that lactose and/or mannitol having excellent dispersibility and proper solubility is used as a sugar.

Though it varies depending on the quality and quantity of the active ingredient to be used, the sugar may be used in the inventive preparation in an amount of at least 50 w/w%, preferably 80 w/w% or more, more preferably 90 w/w% or more, based on the total solid components.

According to the present invention, 0.12 to 1.2 w/w% of agar is used based on the solid components (namely an active ingredient, sugars and the like). By the addition of agar, the following advantages are obtained.

(1) Because of the nature of aqueous agar solution to solidify rapidly into the form of a jelly at room temperature, the aforementioned suspension solidifies in a jelly form within a short time when it is filled in a mold, thus rendering possible prevention of precipitation of solid components in the suspension and formation of a uniform structural body having a desired hardness.

(2) Agar itself also has an effect to improve strength of the pharmaceutical preparation by forming a part of the structural body.

(3) Since the suspension is solidified in the form of a jelly, expansion of the dried surface in the drying step under a reduced pressure condition can be suppressed, thus rendering possible prevention of hardness reduction and irregular shape which are generated by the expansion.

(4) When drying is effected especially under a reduced pressure or with aeration, agar molecules are partly shifted to the upper surface of the preparation together with water molecules, thus resulting in the improvement of strength of the preparation surface structure.

(5) Since the suspension solidifies rapidly into the form of a jelly after its filling in a mold, irregularity in shape does not occur, thus rendering possible easy operations thereafter such as transfer of the mold, drying and the like.

Though gelatin and the like are also known as substances which solidify into the form of a jelly, a desirable preparation may not be obtained when these substances are used because of their inferior operabilities such as inappropriate temperature for jelly-like solidification and prolonged period of time necessary for the solidification, as well as inappropriate hardness and solubility of the resulting preparation after its drying.

Though types of agar are not particularly limited, those listed in the Japanese Pharmacopoeia may be used preferably. Examples of the listed agar include agar powders PS-7 and PS-8 (manufactured by Ina Shokuhin).

Agar may be used in an amount of from 0.12 to 1.2 w/w%, preferably from 0.2 to 0.4 w/w%, based on the solid components.

In order to produce the structural body of the present invention, a sugar comprising lactose and/or mannitol is suspended in an aqueous agar solution, filled in a mold, solidified into a jelly-like form and then dried. The aqueous agar solution may have a concentration of from 0.3 to 2.0%, preferably from 0.3 to 0.8%. The aqueous agar solution may be used in such an amount that the blending ratio of agar based on the solid components becomes 0.12 to 1.2 w/w%, but preferably 40 to 60 w/w% of agar solution based on the solid components.

Concentration of the aqueous agar solution if smaller than 0.3% would bear no advantageous effect of the agar blending. Also, the concentration if larger than the above range would entail delay in the disintegration rate of the resulting preparation in the buccal cavity.

Active ingredients to be applied to the preparation of the present invention are not particularly limited, provided that they are able to be dissolved or suspended in the aqueous agar solution, with their preferred examples including drugs for use in patients having difficulty in swallowing tablets, the aged and children; drugs for use in patients who require drug taking without water during daily life; preparations for use in patients whose water drinking is limited; and drugs for use in potions.

Illustrative examples of drugs having high utility values include:

serotonin $5HT_3$ receptor antagonists such as (R)-5-[(1-methyl- 3-indolyl)carbonyl]-4,5,6,7-tetrahydro-1H-benzimidazole hydrochloride and salts thereof, ondansetron, granisetron and the like,
non-steroidal anti-infammatory drugs such as indometacin, ibuprofen, ibufenac, alclofenac, diclofenac, mefenamic acid, flurbiprofen, flufenamic acid, ketoprofen, phenylbutazone, methyl salicylate and the like,
steroidal anti-infammatory drugs such as cortisone, hydrocortisone, prednisolone, dexamethasone, betamethasone dipropionate, betamethasone valerate, prednisolone, triamcinolone, fluocinolone acetonide and the like, diuretic drugs such as bendroflumethiazide, polythiazide, methyclothiazide, trichlormethiazide, cyclopenthiazide, pentylhydrochlorothiazide, hydrochlorothiazide, bumetanide and the like,
antipsychotic drugs such as emonapride, diazepam, nitrazepam, flunitrazepam, lorazepam, prazepam, fludiazepam, clonazepam, chlorpromazine hydrochloride, reserpine, clofluperol, trifluperidol, haloperidol, moperone and the like, hypnotic drugs such as barbital, thiopental, phenobarbital, cyclobarbital and the like,
antiepileptic drugs such as ethosuximide, sodium valproate, acetazolamide, meprobamate and the like,
antiparkinsonism drugs such as chlorzoxazone, levodopa and the like,
antiemetic drugs such as metoclopramide, metoclopramide hydrochloride and the like,
hormone drugs such as insulin, testosterone, methyltestosterone, progesterone, estradiol and the like, analgesic drugs such as morphine, aspirin, codeine, acetanilide, aminopyrine and the like,
sulfa drugs such as sulfamine, sulfamonomethoxine, sulfamethizole and the like,
coronary vasodilators such as nitroglycerin, isosorbide dinitrate, pentaerythrityl tetranitrate, propatylnitrate, dipyridamole, papaverine HCl and the like,
$H_2$ receptor antagonists such as famotidine, cimetidine, ranitidine HCl, roxatidine acetate HCl and the like,
antiarrhythmic drugs such as ajimalin, pindolol, propranolol, quinidine, amrinone, milrinone and the like,
cardiotonic drugs such as caffeine, digoxin, digitoxin and the like,
calcium antagonists such as nicardipine HCl, diltiazem HCl, nivadipine, nifedipine, nitrendipine, nisoldipine, nimodipine, niludipine and the like,
antihistaminic drugs such as diphenhydramine HCl, carbinoxamine, diphenylpyrallin, phenbenzamine, chlorpheniramine maleate, brompheniramine maleate, diphenylimidazol, clemizole and the like,
antibiotics such as tetracycline, oxytetracycline, metacycline, doxycycline, minocycline, chloramphenicols, erythromycins, lincomycin, penicillin G, clindamycin, kanamycin, chloramphenicol, fradiomycin, streptomycin, gentamycin and the like,
antitumor drugs such as 5-fluorouracil, uracil, cytarabine, floxuridine, busul#an, actinomycin, bleomycin, mitomycin and the like,
antidiabetic drugs such as glibenclamide and the like, gout treating drugs such as allopurinol, colchicine, benzbromarone and the like,
antiallergic drugs such as ketotifen fumarate, sodium cromoglicate, amlexanox and the like,
antihypertensive drugs such as clonidine, guanethidine sulfate, amosulalol HCl, alacepril, delapril HCl, enalapril maleate and the like,
central nervous system acting drugs such as indeloxazine HCl, tiapride HCl, bifemelane HCl and the like, skeletal muscle relaxants such as sodium dantrolene and the like,
antispasmodic drugs such as eberidine HCl, tizanidine HCl, butylscopolamine, atropine methylbromide and the like,
antihyperlipemic drugs such as simvastatin, sodium pravastatin and the like,
bronchodilators such as formoterol fumarate, salbutamol sulfate, procaterol HCl and the like,
α-adrenergic receptor blockers such as tamsulosin hydrochloride and prazasin,
blood sugar lowering drugs,
oral contraceptives, and
animal drugs having antipyretic-analgesic-antiinflammatory activities, peptic antiulcer activities and the like or animal organ drugs for treating reproductive organ and the like.

Active ingredients are not particularly limited, and not only pharmaceutical drugs but also various other substances can be applied to the preparation of the present invention making use of its characteristic nature, which include for example diagnostic drugs such as a contrast medium and the like, healthy food, physiologically functional food and buccals such as a bad breath eliminating drug, a dental plaque disclosing agent and the like.

The active ingredient may be used in an amount of 50 w/w% or less, preferably 20 w/w% or less, more preferably 10 w/w% or less, based on the total solid components, though it varies depending on the nature of each active ingredient to be used.

In general, preferred active ingredients to be applied are those which do not generate unpleasant taste at the time of their dissolution. When a component which generates unpleasant taste is used, it is preferable to employ a proper taste-concealing treatment.

In addition, if necessary, the aqueous agar solution may further have a perfume (menthol, for instance), a sweetener (Aspartame (trade name), for instance), a coloring agent, an stabilizer, a preservative and the like.

The solid preparation of the present invention may have a density approximately in the range of from 400 to 1,000 mg/ml, though it varies depending on the blending ratio of components. A density of from 600 to 900 mg/ml is preferable in view of the relationship between strength and solubility of the solid preparation.

The solid preparation of the present invention has such a sufficient strength for the handling and, therefore, can be put into practical use in the same manner as the case of usual tablets. The term "a sufficient strength for the handling" as used herein means a strength which can withstand at least the usual Press Through Pack (blister packaging), and such a strength will also withstand other handling such as delivery, carrying and the like.

Hardness in the lengthwise direction of tablets may be used as an index of the strength which is applicable to Press Through Pack (blister packaging), namely a strength necessary to take out a preparation by pushing it out of a cover sheet of usual Press Through Pack (blister packaging). Such a hardness varies depending on the size and shape of tablets and may preferably be 1.0 kg or more when the tablet has a diameter of about 8.0 nun, 1.5 kg or more for a diameter of about 10.0 mm and 2.0 kg or more for a diameter of about 12.0 mm. The solid preparation of the present invention has a strength which can fully withstand its taking out from Press Through Pack (blister packaging) regardless of its size.

The term "intrabuccally disintegrating property" as used herein means a practically sufficient disintegration or solubilization of the preparation by saliva in the buccal cavity without taking water. The term "practically sufficient disintegration or solubilization" means that the preparation disintegrates or dissolves generally within approximately 5 to 20 seconds in the buccal cavity, though there are individual variations.

The structural body of the inventive preparation chiefly made of a sugar rapidly becomes brittle due to saliva in the buccal cavity and gradually disintegrates or solubilizes, and the disintegration or solubilization becomes more quick when an intrabuccal pressure, namely a pressure between the upper jaw and tongue, a "licking" movement of tongue, or the like, is applied to the preparation.

The preparation of the present invention does not show rapid disintegration, because its disintegration in water by a tablet disintegration test is approximately 1 to 2 minutes, though it varies depending on the shape. As described above, however, the inventive preparation has a practically sufficient disintegrating or solubilizing property in the buccal cavity.

A person of parched mouth or having a small quantity of saliva in the buccal cavity may use the inventive preparation with the aid of cold or hot water in an amount sufficient to wet the buccal cavity.

Also, the inventive preparation may be swallowed together with a small amount of water after the preparation is disintegrated or solubilized in the buccal cavity or under a partly disintegrated or solubilized condition. Even by such a way of drug-taking, merits of the preparation of the present invention such as easy swallowing, small amount of water to be used and the like can be given.

Of course, the inventive preparation can be taken together with water with no problems similar to the case of usual tablets. The preparation of the present invention can be used by any of these drug-taking means in accordance with each patient's choice or condition, provided that there are no limitations with respect to the active ingredient contained therein.

The following describes a process for the production of the preparation of the present invention.

An aqueous agar solution is prepared by the usual way, for example, by adding water to agar powder and dissolving the agar by heating.

Lactose and/or mannitol and an active ingredient are added to the aqueous agar solution to obtain a uniform suspension. If necessary, a sweetener, a perfume, a coloring agent, a preservative and the like may also be added optionally.

Next, the thus obtained suspension is filled in a mold in the usual way. Filling may be carried out at around room temperature. The filling temperature if too high would require a prolonged period of time for the solidification of the suspension into a jelly form, and the temperature if too low would disturb smooth filling due to solidification of the suspension prior to its filling. The temperature may preferably be in the range of from 15° to 30° C.

The mold to be used is not particularly limited, and those made of metals or resin films may be used. Preferred mold is a resin film sheet having a number of hollows, which is used for the enclosure of tablets by Press Through Pack (blister packaging).

After filling and drying the suspension in the resin film sheet, a cover sheet for use in usual Press Through Pack (blister packaging) is adhered to the resulting resin film sheet, thereby easily obtaining packages of the solid preparation of the present invention. The material of the sheet has no particular limitation, and may be selected from polypropylene, polyvinyl chloride, polyvinylidene chloride and the like.

Though the shape of the mold is not particularly limited, the hollow of the mold may preferably have a globular shape.

Since the suspension filled in the mold solidifies into a jelly form within a short period of time, subsequent shifting and transfer of the mold or drying step can be made easily.

The suspension surface solidifies within 1 to 2 minutes at room temperature to form a predetermined shape, though the time varies depending on the size and shape of the preparation. If necessary, the suspension can be solidified into a jelly form within more shorter time at a low temperature.

Next, the preparation thus solidified into a jelly form is dried. Drying may be effected by any means, provided that it does not spoil characteristics of the solid preparation of the present invention. Preferably, the drying may be effected under reduced pressure or with aeration. The reduced pressure or aeration drying may be carried out at a temperature within such a rage that the preparation solidified into a jelly form does not freeze or re-dissolved, preferably at about 25° to 35° C. in the case of reduced pressure drying or about 3° to 15° C. in the case of aeration drying. In the case of reduced pressure drying, it may be effected near vacuum condition of −750 mmHg or below.

Drying time may be optionally decided depending on the drying method, drying condition and the size and shape of the preparation. For example, it may be 2 to 5 hours in the case of reduced pressure drying or 1 to 6 days in the case of aeration drying.

INDUSTRIAL APPLICABILITY

The solid preparation of the present invention has the following utility.
(1) It shows practically sufficient disintegration or solubilization in the buccal cavity without water and can be swallowed easily (easy to administer).
(2) Since means to take the preparation can be selected at will according to each person's ability, choice and condition (e.g., without water, with the aid of a small amount of water or together with water similar to the case of tablets), improvement in the compliance can be expected.
(3) Since it does not stick on the hand when taken out of its package similar to the case of usual tablets due to its resistance against moisture, it can be handled easily.
(4) It can be taken in correct dose, because it is uniform in both weight and active ingredient content and can be used with no measuring effort at the time of its use or without causing spilling when taken out of its package.
(5) It can be taken out from its package easily, because it has a sufficient strength for the handling and, therefore, can be packaged by any packaging means for easy to take out which is commonly applied to tablets (e.g. Press Through Pack (blister packaging)).
(6) It can be handled in the same manner as commonly used tablets even at the time of its packaging, transferring or carrying.

In consequence, the solid preparation of the present invention is a new dosage form having high practicability, because it can be taken easily due to its practically sufficient disintegration or solubilization in the buccal cavity even without water, can be handled easily in the same manner as commonly used tablets and, especially, is applicable to the aged, patients having difficulty in swallowing, and children. In addition, the preparation of the present invention can be used advantageously by persons who require drug-taking during their daily life, because it can be carried, easily taken out from its package and swallowed without water.

Also, the production process of the preparation of the present invention is effective in industrially manufacturing the aforementioned useful solid preparation. The production process of the present invention is characterized in that an appropriate concentration of aqueous agar solution is used in an amount of from 40 to 60 w/w% based on solid components, thereby effecting quick solidification of a suspension, which is quantitatively filled in a mold, into a jelly form at room temperature. This renders possible not only easy handling of the mold in the subsequent production steps but also production of a preparation having desired strength and intrabuccally disintegrating function, which is uniform in its weight and active ingredient content, has no irregularity in its shape and is uniform in its inner structural body.

In addition, since the drying step is effected when the suspension is solidified into a jelly form, irregularity in shape does not occur, special apparatus is not required and a uniform preparation from which water is thoroughly removed can be obtained even by inexpensive and simple reduced pressure drying or aeration drying, thus resulting in high industrial productivity.

Since plastic containers for Press Through Pack (blister packaging) can be used as the mold in the production process of the present invention, Press Through Pack (blister packaging) can be obtained easily by adhering cover sheets to the containers in the usual way after drying of the jellied suspension.

The following illustratively describes utility of the solid preparation of the present invention.

(1) Disintegration or solubilization property

Disintegration or solubilization of the solid preparation of the present invention in water was measured in accordance with the tablet disintegration test (The Japanese Pharmacopoeia). Each of the data shown in Table 1 is an average of 6 tablets. Disintegration time in the buccal cavity (average of 10 volunteers) is also shown in the table.

TABLE 1

| Tablet disintegration test | |
|---|---|
| Example No. of the present invention | Results of tablet disintegration test |
| Example 1 | 23 seconds |
| 2 (a)*1 | 13.6 |
| 2 (b)*2 | 29.8 |
| 3 | 28 |
| 4 | 58 |
| 5 | 34 |
| 6 | 49 |
| 7 | 29 |
| 8 (a) | 60.3 |
| 9 (a) | 51.5 |
| 10 | 106.8 |

Note
*1 Disintegration time in the buccal cavity in Example 2 (a) was found to be 10 seconds.
*2 Disintegration time in the buccal cavity in Example 2 (b) was found to be 11 seconds.

Thus, the solid preparation of the present invention showed about 13 to 120 seconds of disintegration time by the tablet disintegration test. Though there were individual variations, disintegration time in the buccal cavity was approximately 5 to 20 seconds.

(2) Hardness

Hardness of the preparation of the present invention was measured using a hardness meter. The results are shown in Tables 2 and 3.

TABLE 2

| (1) Uniformity of hardness (lengthwise direction) | | |
|---|---|---|
| | Example 8 (a) | Example 9 (a) |
| No. 1 | 2.1 kg | 2.4 kg |
| 2 | 1.8 | 2.6 |
| 3 | 2.2 | 2.8 |
| 4 | 2.0 | 2.2 |
| 5 | 2.1 | 2.2 |
| 6 | 2.0 | 2.4 |
| 7 | 1.6 | 3.0 |
| 8 | 2.0 | 2.4 |
| 9 | 2.3 | 2.4 |
| 10 | 2.2 | 2.1 |
| Maximum value | 2.3 | 3.0 |
| Minimum value | 1.6 | 2.1 |
| Average value | 2.02 | 2.45 |
| RSD (%) | 10.1% | 11.4% |
| Preparation diameter | about 9.5 mm | about 9.5 mm |

$$RSD\% = \frac{\text{standard deviation}}{\text{average}} \times 100$$

TABLE 3

| (2) Hardness (average value) | | | | | |
|---|---|---|---|---|---|
| Example No. | Hardness (average of 10 tablets) kg | | | | Tablet diameter |
| Example 1 | (lengthwise direction) | 2.9 | (crosswise direction) | 3.4 | about 9.9 mm |
| 2 (a) | (lengthwise direction) | 1.82 | (crosswise direction) | 2.87 | about 7.7 mm |
| 2 (b) | (lengthwise direction) | 2.58 | (crosswise direction) | 3.28 | about 9.9 mm |
| 3 | (lengthwise direction) | 2.5 | (crosswise direction) | | about 10.0 mm |
| 4 | (lengthwise direction) | 2.1 | (crosswise direction) | | about 10.0 mm |
| 5 | (lengthwise direction) | 2.0 | (crosswire direction) | | about 10.0 mm |
| 6 | (lengthwise direction) | 1.8 | (crosswise direction) | | about 10.0 mm |
| 7 | (lengthwise direction) | 1.8 | (crosswire direction) | | about 10.0 mm |
| 10 | (lengthwise direction) | 3.25 | (crosswire direction) | | about 9.5 mm |

Each of the solid preparations of the present invention has a lengthwise direction hardness which is applicable to Press Through Pack (blister packaging). Also, the hardness was small in its dispersion and the uniformity of hardness was equivalent to those of usual tablets.

(3) Weight deviation and uniformity of active ingredient

Weight deviation of tablets obtained in Example 11 and uniformity of the content of famotidine used as an active ingredient were measured. Quantity of famotidine was measured by HPLC and expressed as % of its calculated value. The results are shown in Table 4.

TABLE 4

| Weight deviation and content uniformity tests | | |
|---|---|---|
| Preparation No. | Preparation weight | Measured famotidine value |
| No. 1 | 77.40 mg | 99.20% |
| 2 | 77.00 | 100.60 |
| 3 | 78.10 | 99.10 |
| 4 | 77.30 | 98.50 |
| 5 | 77.20 | 99.90 |
| 6 | 76.90 | 101.10 |

TABLE 4-continued

Weight deviation and content uniformity tests

| Preparation No. | Preparation weight | Measured famotidine value |
| --- | --- | --- |
| 7 | 77.10 | 101.90 |
| 8 | 76.30 | 100.30 |
| 9 | 76.60 | 99.10 |
| 10 | 76.90 | 99.40 |
| Average | 77.08 | 99.91 |
| Standard deviation | 0.48 | 1.06 |
| Maximum value | 78.10 | 101.90 |
| Minimum value | 76.30 | 98.50 |
| Maximum − minimum | 1.80 | 3.40 |
| RSD (%) | 0.63 | 1.06 |

Results of the above weight deviation test and content uniformity test confirmed that the solid preparation of the present invention has sufficiently practical uniformities in its weight and active ingredient content.

(4) Push out test of Press Through Pack (blister packaging)

Using the Press Through Pack (blister packaging) containing the solid preparation of the present invention obtained in Example 9 (a) and (b), damage on the preparation inflicted by its push and take out from the cover sheet was examined.

The number of tablets showing "crack, break or chip" formed when they were pushed out from the cover sheet was observed by the naked eye. The results are shown in Table 5 as the number of preparations (tablets) having "crack, break or chip" per tested numbers (tablets).

TABLE 5

Press Through Pack (blister packaging) push out test

| Examiners | A | B | C | D | E | F | total |
| --- | --- | --- | --- | --- | --- | --- | --- |
| Example 9 (a) | 0/50 | 0/50 | 0/50 | 0/50 | 0/50 | 0/50 | 0/300 |
| Example 9 (b) | 0/20 | 0/20 | 0/20 | 0/20 | 0/20 | 0/20 | 0/120 |

These results show that the preparation of the present invention does not cause significant "crack, break or chip" when taken out from the Press Through Pack (blister packaging) and therefore has a sufficient strength in terms of its handling.

BEST MODE OF CARRYING OUT THE INVENTION (Production Example)

A preferred example of the process for the production of the preparation of the present invention is given below by way of illustration and not by way of limitation.

Formulation of the inventive preparation

Active ingredient 0.001 to 50.0 parts, preferably 0.01 to 20.0 parts

Lactose and/or mannitol 50.0 to 99.999 parts, preferably 80.0 to 99.9 parts

Sweetener, perfume, coloring proper amounts according to agent and/or preservative etc. the requirement Agar 0.12 to 1.2 parts, preferably 0.2 to 0.4 parts An aqueous solution containing 0.3 to 2.0%, preferably 0.3 to 0.8%, of agar is prepared and the above components are added to the solution and mixed to obtain a suspension. The resulting suspension is filled in a mold at room temperature and then dried under either of the following conditions to obtain the preparation of the present invention.

Drying conditions (i) Two to five hours of reduced pressure drying at a temperature of preferably from 25° to 35° C., more preferably around 30° C., under a pressure of −700 to −760 mmHg.

(ii) One to six days, preferably 2 to 3 days, of aeration drying at a temperature of preferably from 3° to 15° C., more preferably from 5° to 10° C.

The following examples are provided to further illustrate the intrabuccal preparation of the present invention in which the above production example is employed.

EXAMPLE 1

To 100 parts of 0.4% agar aqueous solution were added 10 parts of famotidine, 89 parts of lactose, 100 parts of mannitol and 0.5 part of aspartame, followed by mixing to obtain a suspension. A 255 mg portion of the thus prepared suspension was filled in a mold of 10.5 mm in diameter and dried at 30° C. under −760 mmHg to remove water, thereby obtaining a solid preparation. The thus obtained solid preparation showed a sufficient disintegration ability in the buccal cavity and was able to be swallowed easily without water.

EXAMPLE 2

To 85 parts of 0.4% agar aqueous solution were added 20 parts of famotidine, 87 parts of lactose, 60 parts of mannitol, 1 part of l-menthol and 2 parts of aspartame, followed by mixing to obtain a suspension. The thus prepared suspension was filled (a) in a mold of 8.0 mm in diameter in an amount of 123 mg or (b) in a mold of 10.5 mm in diameter in an amount of 255 mg, and dried at 30° C. under −760 mmHg to remove water, thereby obtaining solid preparations. Diameter and thickness of the thus obtained tablets were (a) 7.7 mm in diameter and 3.1 mm in thickness and (b) 9.9 mm in diameter and 3.7 mm in thickness.

EXAMPLES 3 to 7

Famotidine, lactose and mannitol in respective amounts (weight ratio) as shown in Table 6 were dispersed in 85 parts of 0.4% agar aqueous solution which has been maintained at 35° to 40° C., and the resulting suspension was filled in 200 µl portions in a sheet for Press Through Pack (blister packaging) having hollows of 11 mm in diameter and dried at 30° C. under −760 mmHg. The thus obtained tablets had a diameter of about 10 mm.

TABLE 6

Blending ratio of the preparations of Examples 3 to 7

| | Blending ratio | | |
| --- | --- | --- | --- |
| Example No. | Famotidine | Lactose | Mannitol |
| 3 | 20.0 | 150.0 | 0.0 |
| 4 | 20.0 | 120.0 | 30.0 |
| 5 | 20.0 | 90.0 | 60.0 |
| 6 | 20.0 | 60.0 | 90.0 |
| 7 | 20.0 | 0.0 | 150.0 |

EXAMPLE 8

In 85 parts of 0.6% agar aqueous solution were dissolved 1.5 parts of aspartame and 1.0 part of sodium citrate, followed by the addition of 10 parts of famotidine, parts of lactose, 20 parts of mannitol, 1.4 parts of a perfume and 0.1 part of a coloring agent and subsequent mixing to obtain a suspension. The thus prepared suspension was filled in (a) 255 mg portions and (b) 510 mg portions in hollows of respective two different sheets (made of polypropylene) for Press Through Pack (blister packaging). By carrying out 3 days of drying with aeration at 5° C., solid preparations were obtained.

The size of the thus obtained preparations were (a) about 9.5 mm in diameter and about 4.2 mm in thickness and (b) about 12.0 mm in diameter and about 5.2 mm in thickness.

EXAMPLE 9

A suspension prepared in the same manner as described in Example 8 except for the use of 8.43 parts of perfume was filled in (a) 255 mg portions and (b) 510 mg portions in hollows of respective sheets for Press Through Pack (blister packaging) and dried in the same manner as described in Example 8 to obtain solid preparations. The size of the thus obtained preparations were (a) about 9.5 mm in diameter and about 4.2 mm in thickness and (b) about 12.0 mm in diameter and about 5.2 mm in thickness.

An aluminum sheet was adhered to each of the solid preparation-containing sheets for Press Through Pack (blister packaging) in the usual way to obtain Press Through Pack (blister packaging).

EXAMPLE 10

A suspension prepared in the same manner as described in Example 8 using 85 parts of 0.6% agar aqueous solution, 10 parts of famotidine, 135 parts of lactose, 20 parts of mannitol, 1.5 parts of aspartame, 1.0 part of sodium citrate, 3.34 parts of a perfume and 0.1 part of a coloring agent was filled in 255 mg portions in hollows of a sheet for Press Through Pack (blister packaging) and dried in the same manner as described in Example 8 to obtain a solid preparation of about 9.5 mm in diameter.

EXAMPLE 11

To 43 parts of 0.4% agar aqueous solution were added 10 parts of famotidine, 63 parts of lactose, 10 parts of mannitol, 1.0 part of aspartame and 1.0 part of sodium citrate to prepare a suspension. The thus prepared suspension was filled in 128 mg portions in hollows of a sheet for Press Through Pack (blister packaging) and dried at 30° C. under −760 mmHg to obtain a solid preparation. Other solid preparations can be produced in the same manner as described in Example 1 or 8 making use of the following formulations.

EXAMPLE 12

| formoterol fumarate | 0.04 part |
|---|---|
| lactose | 79.16 part |
| mannitol | 20.00 part |
| aspartame | 0.50 part |
| agar powder | 0.30 part |
| total | 100.00 parts |

EXAMPLE 13

| nicardipine HCl | 10.0 parts |
|---|---|
| lactose | 148.4 parts |
| mannitol | 40.0 parts |
| aspartame | 1.0 parts |
| agar powder | 0.6 parts |
| total | 200.0 parts |

We claim:

1. An intrabuccally disintegrating solid preparation which comprises an active ingredient, a sugar comprising lactose and/or mannitol, and an agar in an amount of from 0.12 to 1.2 w/w% based on the solid components, said preparation having a density of from 400 mg/ml to 1,000 mg/ml and a sufficient strength to withstand removal from a Press Through Pack (blister packaging) without disintegrating.

2. The solid preparation according to claim 1, wherein said preparation is produced by suspending an active ingredient and a sugar comprising lactose and/or mannitol in a 0.3 to 2.0 w/w% agar aqueous solution used in an amount of 40 to 60 w/w% based on the solid components, filling the suspension in a mold to solidify the suspension into a jelly form, and subsequently drying the jelly.

3. The solid preparation according to claim 2, wherein said drying is effected by reduced pressure drying or aeration drying.

4. A process for producing an intrabuccally disintegrating solid preparation having a sufficient strength for the handling, which comprises suspending an active ingredient and a sugar comprising lactose and/or mannitol in a 0.3 to 2.0 w/w% agar aqueous solution used in an amount of 40 to 60 w/w% based on the solid components, filling the suspension in a mold to solidify the suspension into a jelly form, and subsequently drying the jelly.

5. The production process according to claim 4, wherein said drying is effected by reduced pressure drying or aeration drying.

6. The production process according to claim 4, wherein said mold is a resin film sheet for Press Through Pack (blister packaging) use.

* * * * *